United States Patent [19]

Klutchko et al.

[11] 4,012,411
[45] Mar. 15, 1977

[54] HETEROCYCLIC ANNELATED 1-BENZOXEPIN-5-ONES

[75] Inventors: Sylvester Klutchko, Hackettstown; John Shavel, Jr., Mendham; Max Von Strandtmann, Rockaway, all of N.J.

[73] Assignee: Warner-Lambert Company, Morris Plains, N.J.

[22] Filed: Mar. 3, 1975

[21] Appl. No.: 554,841

[52] U.S. Cl. .................. 260/307 H; 260/302 F; 260/310 R; 260/333; 424/270; 424/272; 424/273

[51] Int. Cl.² .................. C07D 498/04

[58] Field of Search .................. 260/307 H

[56] References Cited
OTHER PUBLICATIONS

Oppolzer et al., C. A. 72, 132589v (1970).

*Primary Examiner*—Raymond V. Rush
*Attorney, Agent, or Firm*—Albert H. Graddis; Frank S. Chow

[57] ABSTRACT

Compounds of the formula:

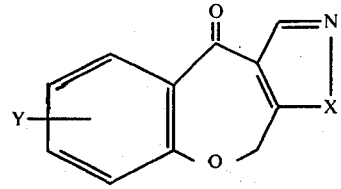

are disclosed wherein X is NH, O or S and the tautomers thereof when X is nitrogen, and Y is hydrogen, lower alkyl, hydroxy, lower alkoxy, chloro, bromo or aryl. These compounds are useful in the management of allergic manifestations such as bronchial asthma.

1 Claim, No Drawings

HETEROCYCLIC ANNELATED 1-BENZOXEPIN-5-ONES

The present invention relates to heterocyclic annelated 1-benzoxepin-5-ones, having the following structural formula:

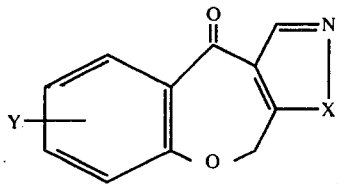

wherein X is NH, O or S and tautomers thereof when X is nitrogen, and Y is hydrogen, lower alkyl, hydroxy, lower alkoxy, chloro, bromo or aryl.

The above compounds exhibit anti-allergic properties. For example, in tests conducted according to procedures described by I. Mota, Life Sciences, 7, 465 (1963) and Z. Ovary, O. Bier, Proc. Soc. Exptl. Biol. Med., 81, 584 (1952), these compounds prevent allergic and asthmatic reactions in rats at a dose of about 25 mg/kg intraperitoneally. These compounds are indicated in the management of allergic manifestations such as asthma, hay fever in mammals, e.g., men. Generally, a dose of 25 mg/kg orally or by injection is indicated to provide symptomatic relief.

These compounds are administered in dosage forms such as tablets or injections. These dosage forms are prepared by compounding the active ingredient with known excipients such as lactose into dosage forms such as tablets by methods well known in the art. For injection, they are suspended in vehicles such as water for injection and compounded with known excipients to form acceptable dosage forms. Alternatively, these compounds may also be administered in the form of aerosols. Such aerosols are also prepared by well known methods in the art, e.g., as described in U.S. Pat. Nos. 2,868,691 and 3,095,358.

The compounds of this invention are prepared by treating hydroxylamine with 2,3-dihydro-5-hydroxy-3-oxo-1-benzoxepin-4-carboxaldehyde. Generally speaking, the reaction is effected at about ambient temperature to the reflux temperature of the solvent employed. The desired reaction product occurs in the form of a precipitate in the reaction mixture and is recovered by conventional procedures.

The starting 2,3-dihydro-3-oxo-1-benzoxepin-4-carboxaldehyde is prepared in accordance with the description set forth in our copending application entitled "4-Substituted-2,3-dihydro-1-benzoxepin-3,5-diones and tautomers," which is filed concurrently herewith. Ser. No. 554,876 filed on Mar. 3, 1975, now allowed.

In the above definitions for Y and in the claims hereafter, lower alkyl and the alkyl position of lower alkoxy are meant to include straight-or branched-chain alkyl groups of 1–6 carbon atoms such as methyl, ethyl, propyl, isopropyl and the like. Aryl is preferably a monocyclic aromatic ring having 6–10 carbon atoms such as phenyl and substituted phenyl.

In order to further illustrate the practice of this invention, the following examples are included. In the examples, temperatures are in degrees Centigrade.

EXAMPLE 1

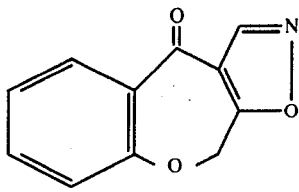

1-Benzoxepino[4,3-d]isoxazol-4(10H)-one. To a slurry of 24.48g (0.12 mole) of 2,3-dihydro-5-hydroxy-3-oxo-1-benzoxepin-4-carboxaldehyde in 1 l. of water added 130ml (0.13 mole) of 1N sodium hydroxide. The resulting solution was treated with solution of 9.04g (0.13 mole) of hydroxylamine hydrochloride in 40ml of water. Solid separated. Methanol (400ml) was added, and the mixture was heated to reflux. Most solid went into solution when a new solid began to separate. After 10 minutes at reflux, the mixture was cooled, filtered, and the filter cake was washed well with water and dried; wt. 20g (78%); m.p. 109°–111°. Recrystallization from ethyl acetate gave pure isoxazole derivative; m.p. 116°–118°.

Anal. Calcd. for $C_{11}H_7NO_3$: C, 65.67; H, 3.51; N, 6.96. Found: C, 65.97; H, 3.61; N, 6.89.

EXAMPLE 2

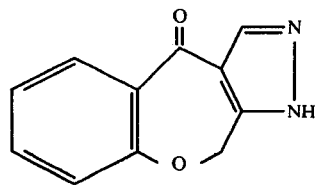

1,10-Dihydro-4H-1-benzoxepino[3,4-c]pyrazol-4-one. A quantity of 10.2g (0.05 mole) of 2,3-dihydro-5-hydroxy-3-oxo-1-benzoxepin-4-carboxaldehyde was added to 60ml of hydrazine hydrate with stirring over a period of 2 minutes. There was a rise in temperature (55°) as partial solution took place. The mixture was stirred for one-half hour, cooled, filtered, and the filter cake was washed with water; wt. 7.5g (75%); m.p. 146°–148°. Recrystallization from ether gave pure pyrazol derivative; m.p. 146°–148°.

Anal. Calcd. for $C_{11}H_8N_2O_2$: C, 65.99; H, 4.03; N, 13.99. Found: C, 65.71; H, 4.15; N, 14.10.

We claim:
1. A compound of the formula:

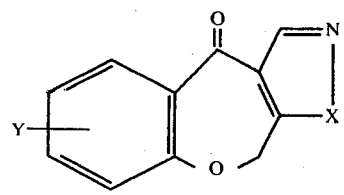

wherein X is oxygen, and Y is hydrogen.